United States Patent [19]

Schenck et al.

[11] Patent Number: 5,702,446
[45] Date of Patent: Dec. 30, 1997

[54] BONE PROSTHESIS

[75] Inventors: Robert C. Schenck, Comfort; C. Mauli Agrawal, San Antonio, both of Tex.

[73] Assignee: Board of Regents, The University of Texas System, Austin, Tex.

[21] Appl. No.: 734,626

[22] Filed: Oct. 18, 1996

Related U.S. Application Data

[63] Continuation of Ser. No. 973,033, Nov. 9, 1992, abandoned.
[51] Int. Cl.$^6$ ...................................................... A61F 2/28
[52] U.S. Cl. ..................... 623/16; 623/22; 623/23; 433/226
[58] Field of Search .................. 623/11, 16, 22, 623/23, 901; 433/226

[56] References Cited

U.S. PATENT DOCUMENTS

| | | | |
|---|---|---|---|
| 4,012,796 | 3/1977 | Weisman et al. | 3/1.91 |
| 4,120,730 | 10/1978 | Trojer et al. | 106/39.6 |
| 4,274,163 | 6/1981 | Malcom et al. | 623/18 |
| 4,279,249 | 7/1981 | Vert et al. | 128/92 D |
| 4,355,426 | 10/1982 | MacGregor | 3/1.4 |
| 4,546,500 | 10/1985 | Bell | 623/1 |
| 4,563,489 | 1/1986 | Urist | 524/21 |
| 4,698,063 | 10/1987 | Link et al. | 623/23 |
| 4,750,905 | 6/1988 | Koeneman et al. | 623/16 |
| 4,795,467 | 1/1989 | Piez et al. | 623/16 |
| 4,795,475 | 1/1989 | Walker | 623/16 |
| 4,804,382 | 2/1989 | Turina et al. | 623/11 |
| 4,920,203 | 4/1990 | Tang et al. | 525/409 |
| 4,938,772 | 7/1990 | Frey et al. | 623/18 |
| 4,978,358 | 12/1990 | Bobyn | 623/23 |
| 5,098,779 | 3/1992 | Kronzler et al. | 623/11 |
| 5,116,377 | 5/1992 | Skripitz et al. | 623/23 |
| 5,250,584 | 10/1993 | Ikada et al. | 623/16 |
| 5,250,585 | 10/1993 | Guggenberger et al. | 523/116 |
| 5,258,029 | 11/1993 | Chu et al. | 623/16 |
| 5,263,986 | 11/1993 | Noiles et al. | 623/16 |
| 5,281,419 | 1/1994 | Tuan et al. | 424/426 |
| 5,376,123 | 12/1994 | Klaue et al. | 623/16 |
| 5,522,895 | 6/1996 | Mikos | 623/16 |

FOREIGN PATENT DOCUMENTS

| | | |
|---|---|---|
| 0 194 192 | 9/1986 | European Pat. Off. . |
| 0 361 896 | 4/1990 | European Pat. Off. . |
| 0 550 875 | 7/1993 | European Pat. Off. . |
| 0 636 377 | 2/1995 | European Pat. Off. . |
| 2 215 209 | 9/1989 | United Kingdom . |
| WO 90/04982 | 5/1990 | WIPO . |
| WO 90/13302 | 11/1990 | WIPO . |

OTHER PUBLICATIONS

Albrektsson and Hansson, "An Ultrastructural Characterization of the Interface Between Bone and Sputtered Titanium or Stainless Steel Surfaces," *Biomaterials*, 7:201–205, May 1986.

Aldinger et al., "Bone Morphogenetic Protein: A Review," *International Orthop. (SICOT)*, 15:169–177, 1991.

(List continued on next page.)

*Primary Examiner*—Paul B. Prebilic
*Attorney, Agent, or Firm*—Arnold, White & Durkee

[57] ABSTRACT

A bone prosthesis having a porous or mesh type mating surface for attachment to bone and at least one continuous hollow internal chamber is disclosed. The prosthesis also includes at least one portal and at least one channel extending from each hollow chamber that allows communication between the chamber of the prosthesis and the mating surface of the device. Biomaterial for enhancing bone growth is injected in fluid form through a portal of the device into a hollow chamber, simultaneous with or after press fitting the prosthesis into the bone. Biomaterial thereby reaches bone mating surfaces through one or more channels. Bony growth at a mating surface of the prosthesis is enhanced, and union of the prosthesis with bone is thereby promoted.

8 Claims, 3 Drawing Sheets

OTHER PUBLICATIONS

Athanasiou et al., "Biodegradable Carriers of GF–β in Rabbit Osteochondral Defects," *39th Annual Meeting, Orthopaedic Research Society*, San Francisco, CA, Feb. 15–18, 1993.

Bobyn et al., "The Optimum Pore size for the Fixation of Porous–Surfaced Metal Implants by the Ingrowth of Bone," *Clinical Orthopaedics and Related Research*, 150:263–270, Jul./Aug. 1980.

Buser et al., "Influence of Surface characteristics on Bone Integration of Titanium Implants. A Histomorphometric Study in Miniature Pigs," *Journal of Biomedical Materials Research*, 25:889–902, 1991.

Cameron et al., "The Rate of Bone Ingrowth into Porous Meal," *J. Biomed. Mater. Res.*, 10:295–302, 1976.

Collier et al., "Bone Ingrowth into Dynamically Loaded Porous–Coated Intramedulllary Nails," *J. Biomed. Mater. Res. Symposium*, 10(7):485–492, 1976.

Collier et al., "Macroscopic and Microscopic Evidence of Prosthetic Fixation with Porous–Coated Materials," *Clinical Orthopaedics and Related Research*, 235:173–180, Oct. 1988.

Cook et al., "Interface Mechanics and Bone Growth into Porous Co–Cr–Mo Alloy Implants," *Clinical Orthopaedics and Related Research*, 193:271–280, Mar. 1985.

D'Alessandro et al., "Purification, Characterization, and Activity of Recombinant Human BMP–5," *Journal of Cellular Biochemistry*, Supplement 15;166, 1991.

Ferguson et al., "Bovine Bone Morphogenetic Protein (bBMP) Fraction–Induced Repair of Craniotomy Defects in the Rhesus Monkey (*Macaca speciosa*)," *Clinical Orthopaedics and Related Research*, 219:251–258, Jun. 1987.

Geesink et al., "Chemical Implant Fixation Using Hydroxyl-Apatite Coatings: The Development of a Human Total Hip Prosthesis for Chemical Fixation to Bone Using Hydroxyl-Apatite coatings on Titanium Substrates," *Clinical Orthopaedics and Related Research*, 225:147–170, 1987.

Geesink, "Hydroxyapatite–Coated Total Hip Prostheses", *Clinical Orthopaedics and Related Research*, 261:39–58, 1990.

Hulbert et al., "Attachment of Prostheses to the Musculoskeletal System by Tissue Ingrowth and Mechanical Interlocking," *J. Biomed. Mater. Res.*, 4:1–23, 1973.

Jansen et al., "Histologic Evaluation of the Osseous Adaptation to Titanium and Hydroxyapatit–Coated Titanium Implants," *Journal of Biomedical Materials Research*, 25:973–989, 1991.

Kellmann et al., "Analysis of the Diurnal Expression Patterns of the Tomato Chlorophyll a/b Binding Protein Genes. Influence of Light and Characterization of the Gene Family," *Photochemistry and Photobiology*, 52(1):pp. 35–41, 1990.

Lee et al., "Healing of Large Segmental Defects in Rat Femurs is Aided by RhBMP–2 Matrix," *J. Biomedical Materials Research*, 28:1149–1156, 1994.

Lind et al., "Transforming Growth Factor–β enhances Fracture Healing in Rabbit Tibiae," *39th Annual Meeting, Orthopaedic Research Society*, San Francisco, CA, Feb. 15–18, 1993.

Lindholm et al., "Bovine Bone Morphogenetic Protein (bBMP) Induced Repair of Skull Trephine Defects in sheep," *Clinical Orthopaedics and Related Research*, 227:265–268, 1988.

Miller et al., "The Induction of Bone by an Osteogenic Protein and the Conduction of Bone by Porous Hydroxyapatite: A Laboratory Study in the Rabbit," *Plastic and Reconstructive Surgery*, 87(1):87–95 , Jan. 1991.

Mizutani and Urist, "The Nature of Bone Morphogenetic Protein (BMP) Fractions Derived from Bovine Bone Matrix Gelatin," *Clinical Orthopaedics and Related Research*, 171:213–223, Nov./Dec. 1982.

Ohgushi et al., "Bone Formation Process in Porous Calcium Carbonate and Hydroxyapatite," *Journal of Biomedical Materials Research*, 26:885–895, 1992.

Oonishi, "Orthopaedic Applications of Hydroxyapatite," *Biomaterials*, 12:171–178, Mar., 1991.

Pachance, "Collagen–Based Devices for Soft Tissue Repair," *Journal of Biomedical Materials Research (Applied Biomaterials)*, 33:35–40, 1996.

Sato et al., "Induced Regeneration of Calvaria by Bone Morphogenetic Protein (BMP) in Dogs," *Clinical Orthopaedics and Related Research*, 197:301–311, Jul./Aug. 1985.

Syftestad and Urist, "Bone Aging," *Clinical Orthopaedics and Related Research*, 162:288–297, Jan./Feb. 1982.

Takagi and Urist, "The Reaction of the Dura to Bone Morphogenetic Protein (BMP) in Repair of Skull Defects," *Ann Surg*, 196(1):100–109, Jul. 1982.

Trope et al., "Fifth:fifty poly (DL glycolic acid–lactic acid) copolymer as a drug delivery system for 5–fluorouracil: a histopathological evaluation." *Canadian Journal of Ophthalmology*, 29(4):168–71, 1994 (Abstract).

Urist et al., "Osteogenetic Competence," *Clinical Orthopaedics and Related Research*, 64:194–220, May/Jun. 1969.

Wlodarski and Reddi, "Importance of Skeletal Muscle Environment for Ectopic Bone Induction in Mice," *Folia Biol*, 34(4):425–434, 1986.

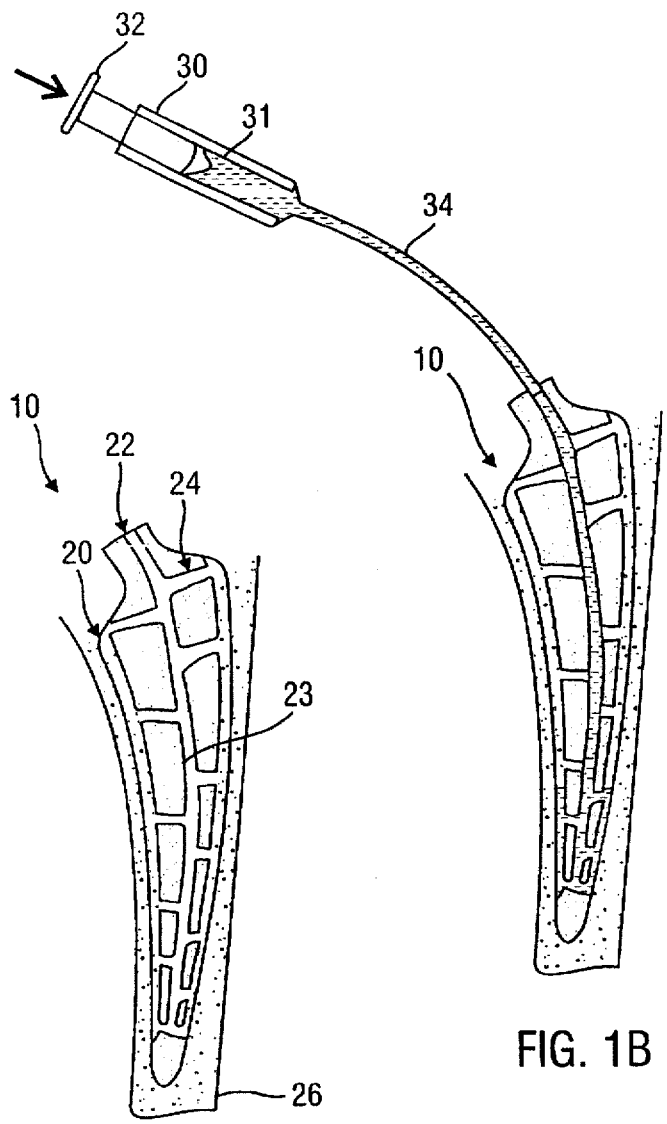
FIG. 1A
FIG. 1B
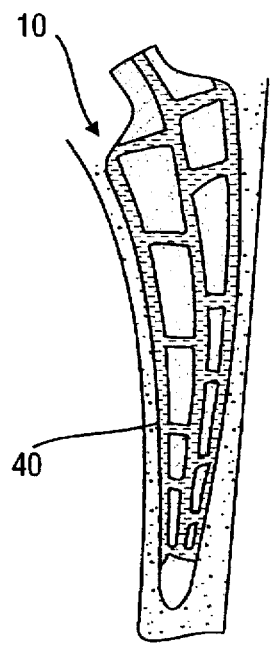
FIG. 1C

BONE PROSTHESIS

This is a continuation of application Ser. No. 07/973,03 filed Nov. 9, 1992 which is now abandoned.

BACKGROUND OF THE INVENTION

1. Field of the Invention

The invention relates generally to prosthetic devices implanted into bone. More specifically, it concerns methods and apparatus related to prostheses with porous or mesh type bone mating surfaces which are press-fit into bone, and which provide means for introduction of biomaterial within the pores or mesh of the surface.

2. Description of the Related Art

Every year several hundred thousand people require artificial hip, knee or shoulder implants (prostheses). Although such total joint prostheses have been in clinical use for decades, they are still plagued with problems of permanent, rigid fixation. Virtually all implants currently in use have a tendency to loosen with time, some to the extent of requiring revision.

There are two main techniques commonly used for fixation: cemented types using bone cement and uncemented or press-fit types. One bone cement in common use is poly(-methyl methacrylate), which is applied in a dough-like state as a grouting agent between the bone and the implant. It flows around the contours of the bone and the implant and into the interstices of cancellous bone. Upon hardening, the cement forms a mechanical interlock between the bone and the implant. In effect, there is no bone in-growth linking bone and prosthesis when bone cement is used. Although bone cement gives good initial fixation, an increase in compliance often occurs due to formation of a soft tissue capsule over time. Thus, the absence of bone in-growth frequently leads to loosening of a bone-cemented prosthesis.

Press-fit prostheses are not implanted with bone cement but rather into a prepared cavity in the bone which closely approximates the prosthetic shape; long term stability of such implants requires bone to form an interlock by growing into the prosthesis at the mating surface. Both porous and mesh type mating surfaces have been employed on press-fit prostheses to enhance fixation in bone, with various materials coated on the surfaces to allow desired bone growth.

Certain osteoconductive materials (e.g., hydroxyl-apatite applied by plasma-spraying) are favored for their durability and bonding strength, but obtaining the desired press-fit at surgery is often associated with problems (Geesink, R. G. T., *Clinical Orthopedics and Related Research*, 261:39–58 (1990)). Further, the cavity prepared in bone to receive the prosthesis is generally not optimally shaped, causing the actual bone contact achieved with insertion of the prosthesis to be only 10–20% of the potential mating surface. The remaining voids between bone and prosthesis, containing little or no osteoconductive material, contribute little to the bone-prosthesis interlock necessary for long-term stability of the prosthesis.

SUMMARY OF THE INVENTION

The present invention serves to remedy the difficulties of prosthetic devices by providing enhanced bone-prosthesis attachment stability. The invention reduces or obviates problems caused by imperfectly formed cavities in bone for press-fit prostheses, as well as problems resulting from damage to previously applied prosthetic coatings. The presently claimed invention comprises methods and apparatus related to a prosthesis having at least one hollow chamber within the prosthesis into which fluid biomaterials may be injected for distribution to the porous or mesh type mating surface of the prosthesis. By allowing delivery of biomaterials in fluid form to the mating surface of a press-fit prosthesis during and after its insertion into a prepared bone cavity, substantially all voids between bone and prosthesis may be filled with biomaterial. Further, fluid biomaterials or those of a soft consistency that are obtainable in a fluid form can be applied to the implanted prosthesis surface after implantation. Thus, the choice of biomaterials is broadened over the relatively hard materials suitable for pre-insertion coating of prostheses.

The claimed invention advantageously allows application of freshly prepared osteoinductive biomaterial (e.g., osteogenic proteins) in fluid form to the implant bone mating surface and adjacent areas after relative movement between the implant and bone has ended during implantation. Subsequent bony ingrowth is then unimpeded by defects in osteoconductive biomaterial coatings. Additionally, the speed and strength of bony growth around the prosthesis is increased because of the use of more growth-promoting materials than those available on pre-coated prostheses, i.e., use of osteoinductive materials alone or in conjunction with osteoconductive materials in contrast to use of osteoconductive material alone (e.g., hydroxyl-apatite plasma sprayed coating).

The term "biomaterial," as it applies to the present invention, includes materials which are osteoconductive (comprising a scaffold or surface suitable for bone growth) or osteoinductive (promoting differentiation of pluripotential mesenchymal cells into osteoblasts). Biomaterials may also be neither osteoconductive nor osteoinductive but merely bioinert or biodegradable materials which act to convey other biomaterials which are osteoinductive (e.g., osteogenic proteins).

Biodegradable materials comprise materials which are separated or chemically altered by natural processes within the body to yield substantially non-toxic degradation products. A bone growth factor is any substance that is required for or that enhances growth of bone. The term "porous" in the present application means having pores allowing the passage of particles up to about 400 μm in maximum dimension but no larger. The terms "mesh" and "mesh type" in the present application refer to mating surfaces having a fine woven character resembling a mesh with interstitial spaces sufficiently large to allow the passage through the mesh of particles up to about 400 μm maximum dimension but no larger.

The term "self-sealing" applies to portals of the present invention which are so designed as to allow the injection of fluid into an interior passage of a prosthesis, but to allow escape of gas only, not fluid, through a filter material of sufficiently small pore size to block fluid movement through the filter. The term "mating surface" or "bone mating surface" in the present application refers to the surface of a bone prosthesis normally in substantial contact with bone when the prosthesis is implanted in bone in an intended manner. "Non-mating" surface is any prosthetic surface which is not "mating surface."

Thus, the present invention also provides for methods for promoting bony ingrowth in a press-fit bone prosthesis. In a preferred embodiment, the method comprises: inserting a press-fit bone prosthesis into a bone, said prosthesis having a non-mating surface, a porous or mesh type mating surface in at least partial contact with the bone, at least one continuous hollow internal chamber, at least one channel extending from each chamber to the mating surface, and at least one portal for conducting fluid into each chamber; and injecting a sufficient amount of an osteoconductive biomaterial through each portal to reach the surface through said channel. In preferred embodiments, at least one portal is on a non-mating surface.

A first embodiment of the present invention is an apparatus for introducing fluid at a bone mating surface, the apparatus comprising: a non-mating surface, a porous or mesh type bone mating surface, at least one and preferably two continuous hollow chambers with each chamber preferably having a termination, at least one channel extending from each chamber to the mating surface, and at least one portal for conducting fluid into each chamber. The portal(s) and termination(s) are preferably on a non-mating surface and the mating surface preferably comprises a metal such as titanium or chrome cobalt. Each portal is preferably self-sealing and adapted to communicate with a syringe pump. Apparatus of the present invention is preferably substantially made of metal, ceramic, polymer, or composite material.

A second embodiment of the present invention is a method for introducing fluid between a bone prosthesis and a bone, the method comprising: inserting a bone prosthesis into a bone, said prosthesis having a non-mating surface, a porous or mesh type mating surface in at least partial contact with the bone, at least one and preferably two continuous hollow internal chambers with each chamber preferably having a termination, at least one channel extending from each chamber to the mating surface, and at least one portal through which fluid may be introduced into each chamber; and injecting fluid through a portal into each chamber so as to force fluid through at least one channel and introduce fluid onto the mating surface between the bone prosthesis and the bone.. At least one portal and the termination for each chamber is preferably on a non-mating surface, and the fluid preferably comprises osteoconductive or osteoinductive biomaterial.

A third embodiment of the present invention is a method for promoting bony in-growth in a press-fit bone prosthesis, the method comprising: inserting a press-fit bone prosthesis into a bone, said prosthesis having a non-mating surface, a porous or mesh type mating surface in at least partial contact with the bone, at least one and preferably two continuous hollow internal chambers with each chamber preferably having a termination, at least one channel extending from each chamber to the mating surface, and at least one portal for conducting fluid into each chamber; and injecting a sufficient amount of an osteoinductive biomaterial through each portal to reach the surface through said channel. At least one portal and the termination for each chamber is preferably on a non-mating surface, and osteoinductive biomaterial is preferably biodegradable and preferably comprises osteogenic protein or bone morphogenic protein.

A fourth embodiment of the present invention is a bone prosthesis having a non-mating surface and a porous or mesh type mating surface, at least one continuous and preferably two hollow internal chambers, each chamber having a termination which is preferably on a non-mating surface, at least one branch channel extending from each chamber to the mating surface of the prosthesis, and a portal through which fluid may be introduced into each chamber. Prostheses of the present invention are preferably substantially made of metal, ceramic, polymer, or composite material.

BRIEF DESCRIPTION OF THE DRAWINGS

FIG. 1A Press-fitting of prosthesis into bone.

FIG. 1B Injection of biodegradable osteoconductive material slurry into prosthesis canal system.

FIG. 1C Filling of porous surface layer of prosthesis with biodegradable osteoconductive material slurry.

DETAILED DESCRIPTION OF THE PREFERRED EMBODIMENTS

Figure 2A:
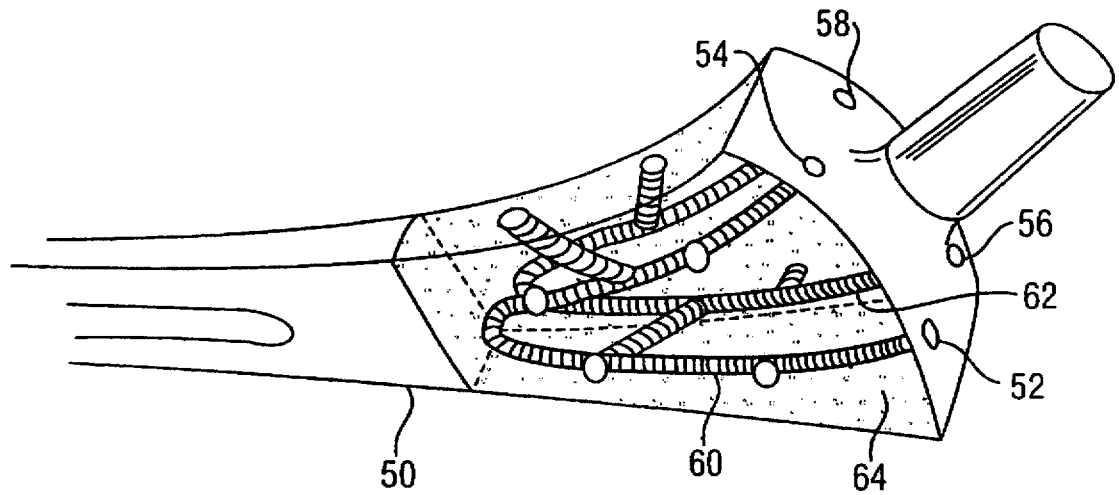
FIG. 2A and FIG. 2B Isometric view of prosthesis with two continuous internal chambers having terminations on a non-mating prosthesis surface.
Figure 2B:
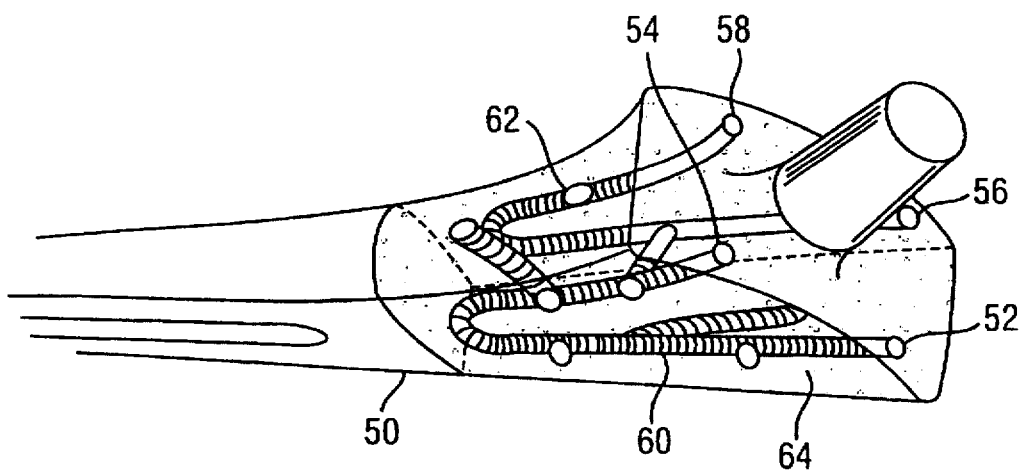
Figure 2C:
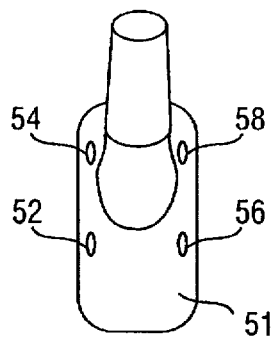
FIG. 2C, FIG. 2D, and FIG. 2E Orthogonal views of prosthesis with two continuous internal chambers having terminations on a non-mating prosthesis surface.
Figure 2D:
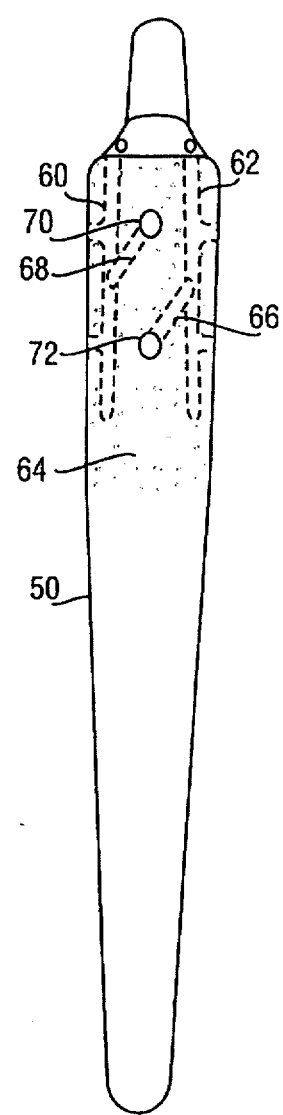
Figure 2E:
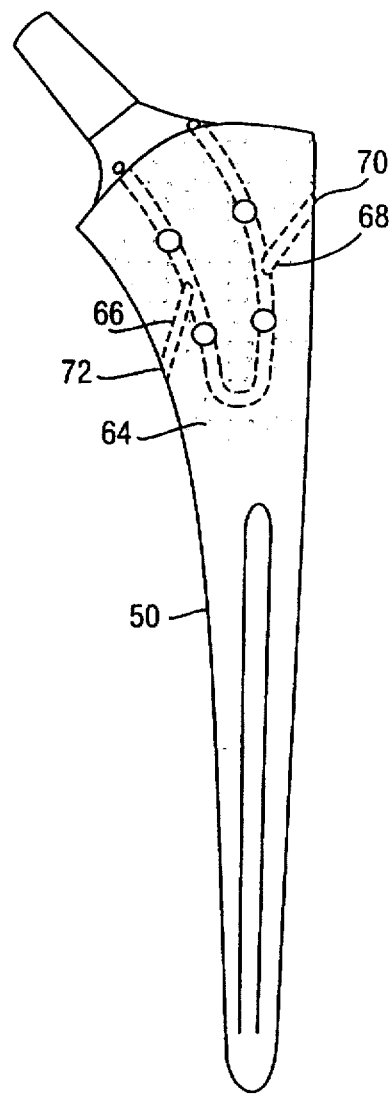

The invention relates to a unique apparatus for introducing fluid between a bone prosthesis and a bone (i.e., at a bone mating surface when the surface is adjacent to a bone), the apparatus comprising a porous or mesh type bone mating surface and at least one continuous hollow chamber, at least one channel extending from each chamber to the surface; and at least one portal on a non-mating surface for conducting fluid into each chamber. Depending on the design of the prosthesis, more than one hollow chamber may be included to shorten the length of channels extending from a chamber to the surface, to improve the flow of fluid injected into the chamber, or to impart desired structural properties to the prosthesis. Further, chambers may terminate within the prosthesis (FIG. 1A, FIG. 1B, and FIG. 1C) or may terminate at the surface of the prosthesis (FIG. 2A, FIG. 2B, FIG. 2C, FIG. 2D, and FIG. 2E). In preferred embodiments of the latter configuration, chamber terminations are located on a non-mating surface. Additionally, they are close enough to the portal for conducting fluid into that chamber so as to allow easy observation of the exiting fluid stream which will issue from the termination when the chamber is slightly over-filled with fluid (see e.g., FIG. 2A, FIG. 2B, FIG. 2C, FIG. 2D, and FIG. 2E). Thus, a visual check is provided to reveal when the entire chamber is filled with fluid injected into that chamber.

In preferred methods of using prostheses with chambers terminating on the prosthesis surface, the termination may be temporarily occluded after the chamber is filled with fluid and while fluid is still being injected into the chamber, thus allowing the fluid within the chamber to be pressurized as it is forced into one or more channels and to the surface of the prosthesis.

With the present invention, the surgeon is able to inject a fluid (solution or slurry) into an internal chamber of a prosthesis through a portal, the fluid filling the chamber and any communicating channel(s) and finally passing out through the pores or mesh at the prosthesis surface. Injection may be simultaneous with or after press fitting of the prosthesis into bone, or both.

The fluid may, most preferably, include a biomaterial. A biomaterial for purposes of describing the present invention is designated as polymer, protein, ceramic or mineral, and may contain bone growth factors. Examples of preferred biomaterials include polylactic acid, polyglycolic acid, polycaprolactone, and various photopolymers which may contain bone morphogenic protein and transforming growth factor β.

In preferred embodiments, the biomaterial as used in conjunction with the present invention encourages the growth and attachment of bone cells (osteocytes). Bone morphogenic protein may be added to enhance cell growth or differentiation or encourage the elaboration of certain cell products. Because biomaterial is injected most preferably either during or after press fitting of the device into bone, direct apposition of the bone to the osteoconductive material filling the pores or mesh is ensured. As the biomaterial is subsequently covered, invaded, or degraded and replaced by normal bone cells, bone will occupy available spaces between the prosthesis and bone, thus providing rigid fixation for the prosthesis.

As described above and in the prophetic examples, the invention provides:

1) a biodegradable, osteoconductive and/or osteoinductive interface between the prosthesis and the bone;
2) substantially complete coverage of porous or mesh type prosthetic surfaces at the prosthesis-bone interface; and
3) the opportunity for the surgeon to choose from a wider range of biomaterials than currently used for prosthetic implants, and to specify the amount, type and composition of biomaterials appropriate for use with each individual prosthesis.

Prostheses of the present invention may be substantially made of metal (e.g., chrome cobalt or titanium), ceramic, polymer or a composite. The porous or mesh type mating surface increases mechanical locking and stabilization of the prosthesis in the bone; in preferred embodiments the mating surface comprises a metal (e.g., chrome cobalt or titanium). At least one channel connects each of one or more continuous hollow internal chambers of the prosthesis with the outer porous or mesh type surface; in preferred embodiments, a plurality of channels are so disposed as to provide efficient distribution of injected fluid to the prosthesis surface while not materially reducing the overall strength of the prosthesis. Each internal chamber is further in communication with space outside and surrounding the prosthesis through at least one portal (preferably self-sealing in some embodiments) through which fluid may be conducted into the internal chamber.

Inasmuch as construction features of prostheses vary, depending on the material(s) used for fabrication and the probable stress to be placed on each prosthesis in use, no fixed specification of surface porosity or dimensions of the internal chamber and branch channels would necessarily be preferred in all applications. Those skilled in the art of prosthesis design would consider factors such as required strength and size of the prosthesis, material(s) available for prosthesis fabrication, flow characteristics, including viscosity and particle size of any biomaterial fluid to be used, possible reinforcement by shape (e.g., with internal ribs) or addition of reinforcing fibers in composite materials.

The preferred particle size range for particulate biomaterial fluids to be used in conjunction with the present invention is less than about 400 μm and most preferably about 150 to 250 μm. Thus, surface porosity and distribution channels are so designed as to allow easy passage to substantially all points of the surface of fluid biomaterials injected at the portal. By way of example, preferred means for introducing fluid (preferably including osteoinductive biomaterial) into the prosthetic internal chamber include a self-sealing portal adapted to communicate with positive displacement pumps (e.g., a syringe pump as in FIG. 1B) or a gas pressure source to force fluid from a storage vessel into the chamber. The biomaterial is preferably in a sufficiently fluid state to allow injection or pumping through the portal into the hollow chamber and distribution via one or more branch channels to the mating surface of the implant (prosthesis). The biomaterial is also preferably biodegradable into substantially non-toxic products in whole or in part.

PROPHETIC EXAMPLE 1

Clinical Applications of the Bone Prosthesis

The present prophetic example is provided to demonstrate a most preferred proposed use of the claimed invention as a bone prosthesis (a press-fit prosthetic device) for the delivery of a fluid biomaterial in an animal. Most preferably, the prosthesis is contemplated for use in humans. A preferred embodiment of the present invention is illustrated in FIG. 1A when the prosthesis 10 is press-fit into the bone 26, the prosthesis-bone interface being at surface 20. Portal 22 is shown at one end of chamber 23, the chamber communicating with a plurality of channels 24, which in turn extend to surface 20. Next, a composition of osteoconductive biomaterial 31 (see FIG. 1B) of suitable fluid consistency and composition for injection under pressure through adapter 34 and portal 22 is prepared and placed in syringe barrel 30 and pressurized for injection by exerting force in the indicated direction on plunger 32.

Considerations including patient positioning, fluid consistency, and closeness of the press fit govern where a prosthesis injection portal should be located in each case. In every case, biomaterial exudes through and onto the porous or mesh type mating surface 20 to form an osteoconductive interface 40 with the bone (FIG. 1C).

In an alternate preferred embodiment, fluid biomaterial 31 may be initially injected into the prosthesis to fill the internal chamber 23 and channels 24 prior to insertion of the prosthesis into bone 26; injection is then completed after placement of the prosthesis within the bone to fill any gaps or voids between prosthesis and bone.

Because according to the present invention, a biomaterial may be injected into a prosthesis simultaneous with or after the device is press fit in the bone, the direct apposition of bone to the osteoconductive material is ensured (FIG. 1C). The presence of biodegradable osteoinductive biomaterial within surface pores further encourages bony growth into the prosthesis with consequent stabilization of the implant.

Note that FIG. 1A, FIG. 1B, FIG. 1C, FIG. 2A, FIG. 2B, FIG. 2C, FIG. 2D, and FIG. 2E are conceptual drawings only; the actual shape and size of the prosthesis will vary according to its intended anatomic location. Further, the exact nature of the porous or mesh type surface could assume several forms, the fundamental requirements being to provide adequate mating surface for the bone and to provide the channels to distribute osteoconductive biomaterial onto the surface of the prosthesis.

PROPHETIC EXAMPLE 2

Fabrication of Prostheses of the Present Invention

Prostheses of the present invention may be fabricated by any of several methods, including drilling the needed inner chamber in a conventionally fabricated prosthesis and subsequently plugging the drill access hole entrance. Communicating branch channels can then be drilled from the prosthesis mating surface to the inner chamber.

In preferred embodiments, drilled branch channels would extend from a mating surface having either a porous or mesh character, connecting the surface at a plurality of points with the inner chamber, whereby fluid flowing from the inner chamber through the branch channels would be distributed over substantially all of the mating surface. In a similar manner, at least one injection portal may be provided by drilling a hole for said portal from a non-mating surface of the prosthesis to communicate with the drilled inner chamber.

PROPHETIC EXAMPLE 3

Embodiments of Prostheses Having More Than One Chamber And Two Portals per Chamber In contrast to the prosthesis of FIG. 1A, FIG. 1B, and FIG. 1C, in which a single internal chamber 23 terminates within the prosthesis, the prosthesis of FIG. 2A, FIG. 2B, FIG. 2C, FIG. 2D, and FIG. 2E provides two internal chambers 60, 62 which terminate on a non-mating prosthesis surface 51. FIG. 2a, FIG. 2B, FIG. 2C, FIG. 2D, and FIG. 2E provides a proposed embodiment of the present invention. For chamber 60, either portal 52 or 54 may be used for fluid injection, and for chamber 62, either portal 56 or 58 may be used for fluid injection. As illustrated by the examples in FIG. 2A, FIG. 2B, FIG. 2C, FIG. 2D, and FIG. 2E preferred embodiments of prostheses 50 of the present invention may comprise two or more chambers 60, 62, each chamber having one or more channels 66, 68 extending from the chamber to distribution points 70, 72 on the mating surface 64. Fluid injected into chamber 60 via portal 52, for example, may emerge from portal 54 as well as from distribution point 70. The latter course is preferred after the former course is established to indicate that chamber 60 is filled with the fluid, thereby reducing the incidence and severity of air-trapping within the fluid passages of the prosthesis 50.

Note that after chamber 60 and channel 68 are filled with fluid injected into portal 52 or 54, fluid flow through channel 68 to distribution point 70 and mating surface 64 may be increased by temporarily occluding the uncovered portal 52 or 54 while maintaining a flow of injected fluid through the other portal 54 or 52. Note also that portals 52, 54, 56, 58 may be self-sealing so as to allow the injection of fluid, but to allow escape of gas only, not fluid, through a filter material of sufficiently small pore size to block fluid movement through the filter.

Changes may be made in the construction, operation and arrangement of the various parts, elements, steps and procedures described herein without departing from the concept and scope of the invention as defined in the following claims.

What is claimed is:

1. A bone prosthesis having a non-mating surface and a porous mesh bone-mating surface, at least one continuous hollow internal chamber, at least one branch channel extending from each chamber to the mating surface of the prosthesis, and a port hole at the non-mating surface through which fluid may be introduced into each internal chamber.

2. A bone prosthesis having a porous mesh bone-mating surface, at least one continuous hollow internal chamber, at least one branch channel extending from each chamber to the mating surface of the prosthesis, and a port hole at a non-mating surface through which fluid may be introduced into each internal chamber.

3. The prosthesis of claim 1 or 2, wherein the prosthesis is substantially made of metal.

4. The prosthesis of claim 1 or 2, wherein the prosthesis is substantially made of ceramic.

5. The prosthesis of claim 1 or 2, wherein the prosthesis is substantially made of polymer.

6. The prosthesis of claim 1 or 2, wherein the prosthesis is substantially made of composite material.

7. The prosthesis of claim 1 or 2, wherein the prosthesis comprises two internal chambers, a portal for each chamber, and a termination for each chamber.

8. The prosthesis of claim 7 wherein the chamber terminations are on the nonmating surface.

* * * * *